United States Patent
Suzuki et al.

(10) Patent No.: US 9,818,926 B2
(45) Date of Patent: Nov. 14, 2017

(54) ULTRASONIC DEVICE AND PROBE AS WELL AS ELECTRONIC APPARATUS AND ULTRASONIC IMAGING APPARATUS

(71) Applicant: SEIKO EPSON CORPORATION, Tokyo (JP)

(72) Inventors: Hironori Suzuki, Nagano (JP); Hiroshi Matsuda, Gifu (JP)

(73) Assignee: Seiko Epson Corporation, Tokyo (JP)

( * ) Notice: Subject to any disclaimer, the term of this patent is extended or adjusted under 35 U.S.C. 154(b) by 355 days.

(21) Appl. No.: 14/807,057

(22) Filed: Jul. 23, 2015

(65) Prior Publication Data

US 2016/0036412 A1 Feb. 4, 2016

(30) Foreign Application Priority Data

Jul. 31, 2014 (JP) .................. 2014-155713

(51) Int. Cl.
| | |
|---|---|
| *B06B 1/06* | (2006.01) |
| *H01L 41/053* | (2006.01) |
| *G01N 29/24* | (2006.01) |
| *G01N 29/26* | (2006.01) |
| *G10K 11/02* | (2006.01) |
| *H01L 27/18* | (2006.01) |
| *H01L 41/09* | (2006.01) |
| *A61B 8/00* | (2006.01) |

(52) U.S. Cl.
CPC .......... *H01L 41/0533* (2013.01); *B06B 1/067* (2013.01); *B06B 1/0629* (2013.01); *G01N 29/2437* (2013.01); *G01N 29/262* (2013.01); *G10K 11/02* (2013.01); *H01L 27/18* (2013.01); *H01L 41/0973* (2013.01); *A61B 8/4427* (2013.01); *A61B 8/4494* (2013.01)

(58) Field of Classification Search
CPC ....... B06B 1/06; B06B 1/0607; B06B 1/0622; B06B 1/0629
USPC ........................................ 310/322, 334, 335
See application file for complete search history.

(56) References Cited

U.S. PATENT DOCUMENTS

2006/0043843 A1* 3/2006 Sugiura ................. B06B 1/0629
310/348
2008/0200811 A1 8/2008 Wakabayashi et al.

FOREIGN PATENT DOCUMENTS

| JP | 2007-235795 A | 9/2007 |
|---|---|---|
| JP | 2008-110060 A | 5/2008 |
| JP | 2008-232801 A | 10/2008 |

(Continued)

*Primary Examiner* — Derek Rosenau
(74) *Attorney, Agent, or Firm* — Global IP Counselors, LLP (57) ABSTRACT

An acoustic matching layer is formed on individual ultrasonic transducer elements on a base. Electric conductors are arranged between adjacent ultrasonic transducer elements, the electric conductors being connected to electrodes of the ultrasonic transducer elements. Protective films overlap the electric conductors. The protective films have smaller moisture permeability than the acoustic matching layer. Wall portions are arranged on the protective films, the wall portions separating portions of the acoustic matching layer that are respectively located on adjacent ultrasonic transducer elements from each other at least in a part of a height range with respect to a height direction from the base, and having an acoustic impedance that is different from the acoustic impedance of the acoustic matching layer.

14 Claims, 7 Drawing Sheets

(56) References Cited

FOREIGN PATENT DOCUMENTS

JP 2013-026735 A 2/2013

\* cited by examiner

ULTRASONIC DEVICE AND PROBE AS WELL AS ELECTRONIC APPARATUS AND ULTRASONIC IMAGING APPARATUS

BACKGROUND

1. Technical Field

The present invention relates to an ultrasonic device as well as a probe, an electronic apparatus, an ultrasonic imaging apparatus, and the like using the same.

2. Related Art

As disclosed in, for example, JP-A-2007-235795, with regard to a so-called bulk-type ultrasonic transducer element, an acoustic matching layer that is in close contact with the surfaces of bulk piezoelectric bodies has been proposed. The acoustic matching layer is divided into pieces respectively corresponding to the piezoelectric bodies. A joint sealing material is filled in a space between adjacent acoustic matching pieces. The acoustic impedance of the joint sealing material is smaller than the acoustic impedance of the acoustic matching body. The joint sealing material has the function of preventing crosstalk between adjacent acoustic matching pieces.

In JP-A-2007-235795, silicone rubber containing filler is used as the joint sealing material. Silicone rubber has moisture permeability. Therefore, moisture passes through the silicone rubber to reach an electrode. The electrode is exposed to moisture. There is a fear that exposure of the electrode to moisture for a prolonged period of time may cause corrosion of the electrode and an increase in electric resistance.

SUMMARY

According to at least one aspect of the invention, it is possible to provide an ultrasonic device that can protect an electric conductor against moisture while preventing crosstalk.

(1) An aspect of the invention is directed to an ultrasonic device including a base, ultrasonic transducer elements that are arranged in an array on the base and that have respective vibration films, an acoustic matching layer formed on the individual ultrasonic transducer elements, electric conductors that are arranged between adjacent ultrasonic transducer elements of said ultrasonic transducer elements when viewed from above in a thickness direction of the base and that are connected to electrodes of said ultrasonic transducer elements, protective films that are arranged on the electric conductors and that have smaller moisture permeability than the acoustic matching layer, and wall portions that are arranged on the protective films and that separate portions of the acoustic matching layer that are respectively located on the adjacent ultrasonic transducer elements from each other at least in a part of a height range with respect to a height direction from the base, the wall portions having an acoustic impedance that is different from an acoustic impedance of the acoustic matching layer.

To transmit ultrasonic waves, the vibration film of an ultrasonic transducer element vibrates ultrasonically. The ultrasonic vibration propagates through the acoustic matching layer and is emitted from an interface of the acoustic matching layer. At this time, the wall portions are arranged between adjacent ultrasonic transducer elements, the wall portions having an acoustic impedance that is different from the acoustic impedance of the acoustic matching layer. Thus, in accordance with the difference in acoustic impedance, interfaces of the acoustic matching layer are formed between the ultrasonic transducer elements. The interfaces prevent propagation of ultrasonic vibration. As a result, transmission of ultrasonic vibration from a single ultrasonically vibrating vibration film toward the vibration film of an ultrasonic transducer element adjacent thereto is prevented. When a single vibration film is vibrating ultrasonically, ultrasonic crosstalk is prevented. Since the moisture permeability of the protective films is smaller than that of the acoustic matching layer, the electric conductors can be more reliably protected against moisture than in the case where the electric conductors are covered with the acoustic matching layer.

(2) In the ultrasonic device, it is preferable that the protective films are arranged at positions on each of the electric conductors where the protective films sandwich a portion of a surface of the electric conductor when viewed from above in the thickness direction of the base. At this time, it is preferable that the ultrasonic device further includes an interconnect that is arranged so as to be surrounded by the portion of the surface of the electric conductor, the protective films that are arranged at positions where the protective films sandwich the portion of the surface of the electric conductor, and the corresponding wall portion. The interconnect can, for example, connect spatially separated electric conductors to each other. At this time, the interconnect is sealed over the entire length thereof. Thus, the interconnect is protected.

(3) It is preferable that a cavity is formed in each of the wall portions. The acoustic impedance of the material for the wall portions is different from the acoustic impedance of the space within the cavity. Therefore, ultrasonic vibration propagates through the wall portion and is reflected by an interface of the cavity. The interface prevents propagation of ultrasonic vibration. As a result, transmission of ultrasonic vibration from a single ultrasonically vibrating vibration film toward the vibration film of an ultrasonic transducer element adjacent thereto can be even more reliably prevented.

(4) It is preferable that the cavity opens in a top surface of the wall portion that is farthest from the base with respect to the height direction, and a bottom of the cavity is located at a predetermined height position from the protective film with respect to the height direction. Since the continuity of the wall portion at its interfaces with the protective film and the interconnect is maintained, a sufficient joining strength of the wall portion with the protective film and the interconnect can be secured.

(5) It is preferable that the protective films are oxide films or nitride films of an inorganic material. Oxide films and nitride films of an inorganic material can reliably provide moisture permeability that is smaller than the moisture permeability of the acoustic matching layer. Accordingly, the protective films can reliably protect the electric conductors against moisture.

(6) It is preferable that the protective films are formed of $Al_2O_3$. $Al_2O_3$ can reliably provide moisture permeability that is smaller than the moisture permeability of the acoustic matching layer. Accordingly, the protective films can reliably protect the electric conductors against moisture.

(7) It is preferable that the wall portions are formed of a material having smaller moisture permeability than the acoustic matching layer. The interconnect is reliably protected against moisture. As a result, it is possible to use a material having high electrical conductivity for the interconnect.

(8) The wall portions may be formed of a permanent resist film. The permanent resist film is formed by baking a resist material. Therefore, the wall portions can be formed with high accuracy and, furthermore, can be realized relatively easily. An increase in manufacturing steps can also be minimized.

(9) It is preferable that the wall portions divide the acoustic matching layer into portions each corresponding to a group of the ultrasonic transducer elements that are connected commonly to a single signal line. The vibration films belonging to a group of ultrasonic transducer elements that are connected commonly to a single signal line vibrate simultaneously in response to the supply of a driving signal. Transmission of ultrasonic vibration from these vibration films toward the vibration films belonging to other groups of ultrasonic transducer elements is prevented.

(10) It is also possible that the wall portions separate portions of the acoustic matching layer from each other, the portions being respectively located on the adjacent ultrasonic transducer elements contained in the group of the ultrasonic transducer elements that are connected commonly to the signal line. Transmission of ultrasonic vibration between simultaneously vibrating vibration films is prevented. Thus, ultrasonic crosstalk between simultaneously vibrating vibration films is prevented.

(11) The ultrasonic device as described above can be used in a state in which it is incorporated into a probe. At this time, it is sufficient if the probe includes the ultrasonic device and a housing that supports the ultrasonic device.

(12) The ultrasonic device can be used in a state in which it is incorporated into an electronic apparatus. At this time, it is sufficient if the electronic apparatus includes the ultrasonic device and a processor that is connected to the ultrasonic device and that processes an output from the ultrasonic device.

(13) The ultrasonic device can be used in a state in which it is incorporated into an ultrasonic imaging apparatus. At this time, it is sufficient if the ultrasonic imaging apparatus includes the ultrasonic device and a display device that displays an image generated based on an output from the ultrasonic device.

BRIEF DESCRIPTION OF THE DRAWINGS

The invention will be described with reference to the accompanying drawings, wherein like numbers reference like elements.

DESCRIPTION OF EXEMPLARY EMBODIMENTS

The following describes embodiments of the invention with reference to the attached drawings. It should be noted that the embodiments to be described hereinafter are not intended to unduly limit the scope of the invention defined by the claims and that not all of the configurations to be described in the embodiments are necessarily essential as the means for achieving the invention.

(1) Overall Configuration of Ultrasonic Diagnostic Apparatus

Figure 1:
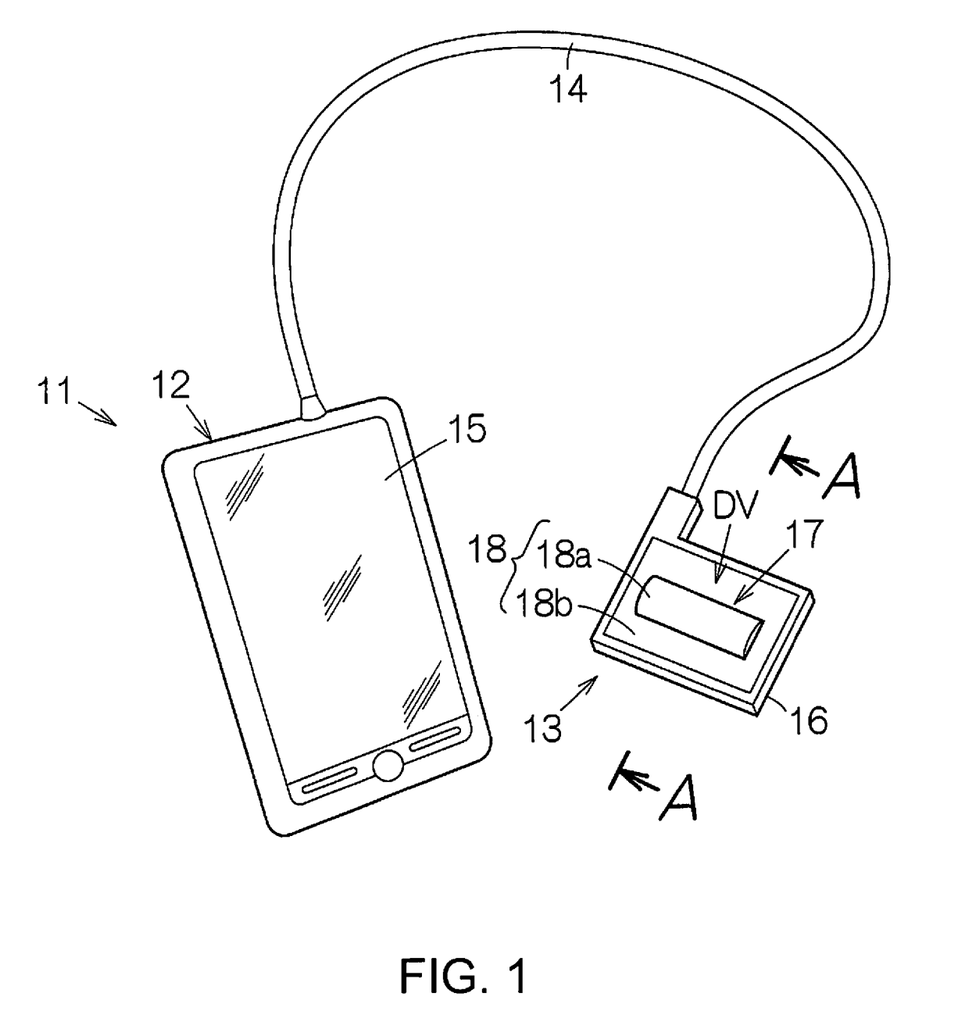
FIG. 1 is an external view schematically showing a specific example, that is, an ultrasonic diagnostic apparatus, of an electronic apparatus according to an embodiment of the invention.

FIG. 1 schematically shows the configuration of a specific example, that is, an ultrasonic diagnostic apparatus (ultrasonic imaging apparatus) 11, of an electronic apparatus according to an embodiment of the invention. The ultrasonic diagnostic apparatus 11 includes a device terminal (processing unit) 12 and an ultrasonic probe (probe) 13. The device terminal 12 and the ultrasonic probe 13 are connected to each other via a cable 14. Electric signals are transmitted through the cable 14 between the device terminal 12 and the ultrasonic probe 13. A display panel (display device) 15 is incorporated into the device terminal 12. A screen of the display panel 15 is exposed at a surface of the device terminal 12. In the device terminal 12, an image is generated based on ultrasonic waves detected by the ultrasonic probe 13. The imaged detection result is displayed on the screen of the display panel 15.

The ultrasonic probe 13 has a housing 16. An ultrasonic device unit DV is fitted in the housing 16. The ultrasonic device unit DV includes an ultrasonic device 17. The ultrasonic device 17 includes an acoustic lens 18. A partial cylindrical surface 18a is formed on an outer surface of the acoustic lens 18. The partial cylindrical surface 18a is surrounded by a flat plate portion 18b. The entire outer perimeter of the flat plate portion 18b is continuously joined to the housing 16. Thus, the flat plate portion 18b functions as a portion of the housing. The acoustic lens 18 may be formed of, for example, a silicone resin. The acoustic lens 18 has an acoustic impedance that is similar to the acoustic impedance of a living body. The ultrasonic device 17 outputs ultrasonic waves from its surface and receives reflected waves of the ultrasonic waves.

(2) Structure of Ultrasonic Device According to First Embodiment

Figure 2:
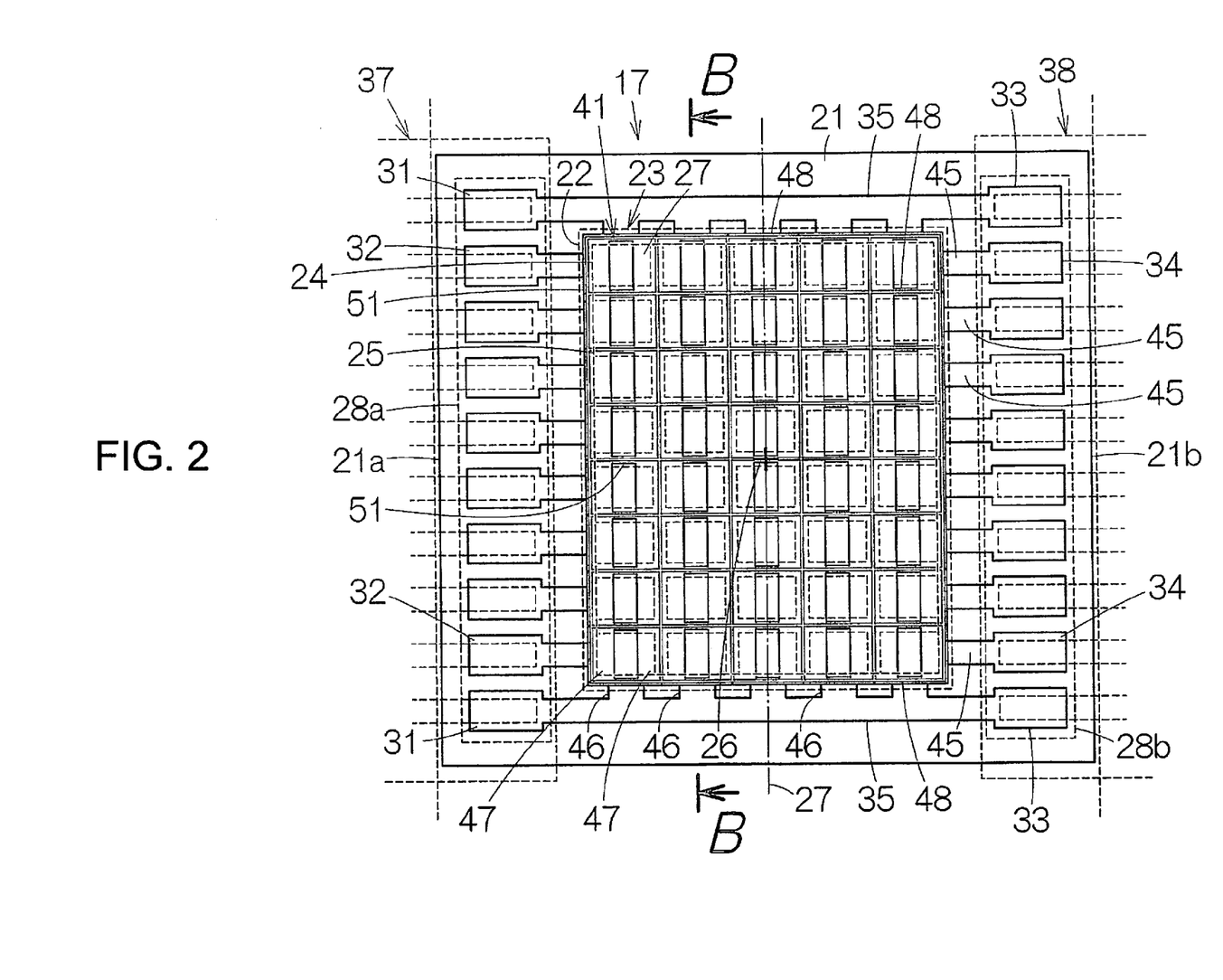
FIG. 2 is an enlarged plan view of an ultrasonic device according to a first embodiment.

FIG. 2 schematically shows a plan view of the ultrasonic device 17 according to a first embodiment. The ultrasonic device 17 includes a base 21. An element array 22 is formed on a surface (first surface) of the base 21. The element, array 22 is constituted by an arrangement of thin-film ultrasonic transducer elements (hereinafter referred to as "elements") 23 that are arranged in an array. The arrangement is in the form of a matrix having a plurality of columns and a plurality of rows. The arrangement may also be established as a staggered arrangement. In a staggered arrangement, a group of elements 23 in each even row can be displaced relative to a group of elements 23 in each odd row by one-half of the column pitch. Either the number of elements in each odd row or the number of elements in each even row may be smaller than the other by one.

Each element 23 includes a vibration film 24. Details of the vibration film 24 will be described later. In FIG. 2, the outline of the vibration film 24 when viewed from above in a direction perpendicular to the film surface of the vibration film 24 (when viewed from above in a thickness direction of a substrate) is shown by dashed lines. The element array 22 defines an element array region 25. The outline of the element array region 25 is formed by a minimum-area quadrilateral circumscribing the vibration films 24 that are located at the outermost perimeter. The element array 22 is formed line-symmetrically with respect to a center line 27 that contains a centroid 26 of the outline. The ultrasonic device 17 is configured as a single ultrasonic transducer element chip (substrate).

The outline of the base 21 has a first side 21a and a second side 21b that are defined by a pair of mutually parallel straight lines and that oppose each other. A first terminal array 28a in a single line is disposed between the first side 21a and the outline of the element array 22. A second terminal array 28b in a single line is disposed between the second side 21b and the outline of the element array 22. The first terminal array 28a can form a single line parallel to the first side 21a. The second terminal array 28b can form a single line parallel to the second side 21b. The first terminal array 28a is constituted by a pair of top electrode terminals 31 and a plurality of bottom electrode terminals 32. Similarly, the second terminal array 28b is constituted by a pair of top electrode terminals 33 and a plurality of bottom electrode terminals 34. One top electrode terminal 31 and one top electrode terminal 33 are respectively connected to the two ends of a single extraction interconnect 35. It is sufficient if the extraction interconnects 35 and the top electrode terminals 31 and 33 are formed line-symmetrically with respect to the center line 27. One bottom electrode terminal 32 and one bottom electrode terminal 34 are respectively connected to the two ends of a single first electric conductor 45. It is sufficient if the bottom electrode terminals 32 and 34 are formed line-symmetrically with respect to the center line 27. Here, the base 21 is formed to have a rectangular outline. The outline of the base 21 may also be square or may be trapezoidal.

A first flexible printed wiring board (hereinafter referred to as "first wiring board") 37 is connected to the base 21. The first wiring board 37 covers the first terminal array 28a. Electrically conductive lines, namely, signal lines are formed at one end of the first wiring board 37, respectively corresponding to the top electrode terminals 31 and the bottom electrode terminals 32. The signal lines are respectively opposed to the top electrode terminals 31 and the bottom electrode terminals 32 and respectively joined thereto. Similarly, a second flexible printed wiring board (hereinafter referred to as "second wiring board") 38 covers the base 21. The second wiring board 38 covers the second terminal array 28b. Electrically conductive lines, namely, signal lines are formed at one end of the second wiring board 38, respectively corresponding to the top electrode terminals 33 and the bottom electrode terminals 34. The signal lines are respectively opposed to the top electrode terminals 33 and the bottom electrode terminals 34 and respectively joined thereto.

A piezoelectric element 41 is formed on the vibration film 24 of each element 23. The piezoelectric element 41 is constituted by a top electrode, a bottom electrode, and a piezoelectric film. In each element 23, the piezoelectric film is sandwiched between the top electrode and the bottom electrode. The bottom electrode, the piezoelectric film, and the top electrode are laid one on top of another in that order. Details of the piezoelectric element 41 will be described later.

A plurality of first electric conductors (signal lines) 45 are formed on the surface of the base 21. The first electric conductors 45 extend parallel to one another in a row direction of the arrangement. One first electric conductor 45 is assigned to corresponding one row of elements 23. One first electric conductor 45 is connected commonly to the elements 23 that are lined up in the row direction of the arrangement. The first electric conductor 45 forms bottom electrodes 43 for the respective elements 23. In this manner, the first electric conductor 45 is disposed inside and outside the regions of the vibration films 24. For example, a laminated film of titanium (Ti), iridium (Ir), platinum (Pt), and titanium (Ti) can be used for the first electric conductors 45. However, other electrically conductive materials may also be used for the first electric conductors 45. The two ends of each first electric conductor 45 are connected to the corresponding bottom electrode terminals 32 and 34, respectively.

A plurality of second electric conductors 46 are formed on the surface of the base 21. The second electric conductors 46 extend parallel to one another in a column direction of the arrangement. One second electric conductor 46 is assigned to corresponding one column of the elements 23. A single second electric conductor 46 is connected commonly to the elements 23 that are lined up in the column direction of the arrangement. Each second electric conductor 46 forms top electrodes for the respective elements 23. The two ends of each second electric conductor 46 are respectively connected to the pair of extraction interconnects 35. The extraction interconnects 35 extend parallel to each other in the row direction of the arrangement. Therefore, all the second electric conductors 46 have the same length. Thus, the top electrodes are connected commonly to the elements 23 of the entire matrix. In this manner, the second electric conductors 46 are disposed inside and outside the regions of the vibration films 24. The second electric conductors 46 can be formed of, for example, iridium (Ir). However, other electrically conductive materials may also be used for the second electric conductors 46. The two ends of each second electric conductor 46 are connected to the respective extraction interconnects 35.

Energization of the elements 23 is switched on a row-by-row basis. A linear scan and a sector scan can be achieved in accordance with this switching of energization. Since the elements 23 in a single row simultaneously output ultrasonic waves, the number of elements in a single row, that is, the number of columns of the arrangement can be determined in accordance with the output level of ultrasonic waves. The number of columns can be set at, for example, about 10 to 15. In FIG. 2, some columns are not shown, and only five columns are shown. The number of rows of the arrangement can be determined in accordance with the extent of the scan range. The number of rows can be set at, for example, 128 or 256. In FIG. 2, some rows are not shown, and only eight rows are shown. The functions of the top electrodes and the bottom electrodes may be reversed. That is to say, it is also possible that while the bottom electrodes are connected commonly to the elements 23 of the entire matrix, the top electrodes are connected commonly to the elements 23 in each row of the arrangement.

First protective films 47 are arranged, on the vibration films 24, in parallel with the second electric conductors 46. The first protective films 47 extend in a longitudinal direction of the second electric conductors 46 so as to have strip shapes. The first protective films 47 have insulating ability and moisture-proofness. The first protective films 47 may be composed of, for example, an oxide film or a nitride film of inorganic matter such as alumina ($Al_2O_3$) or silicon oxide ($SiO_2$). The first protective films 47 have insulating ability. The first protective films 47 are formed separately on both sides of each second electric conductor 46 such that the second electric conductor 46 is sandwiched by the corresponding first protective films 47. That is to say, the first protective films 47 are arranged at positions on the second electric conductor 46 where the first protective films 47 sandwich a portion of the surface of the second electric conductor 46 when viewed from above. Since the second electric conductors 46 cross the first electric conductors 45 on the vibration films 24, the first protective films 47, on the vibration films 24, extend across the first electric conductors 45. In this manner, the first protective films 47 are arranged over the first electric conductors 45. That is to say, the first protective films 47 overlap the first electric conductors 45.

On the base 21, second protective films 48 are formed outside the regions of the vibration films 24. The second protective films 48 extend in a longitudinal direction of the first electric conductors 45 so as to have strip shapes. Each second protective film 48 is disposed between adjacent vibration films 24. The second protective films 48 may be composed of, for example, an oxide film or a nitride film of inorganic matter such as alumina or silicon oxide. The second protective films have insulating ability. The material for the second protective films 48 may be the same as the material for the first protective films 47. The second protective films 48 extend across the second electric conductors 46. In this manner, the second protective films 48 are arranged on the second electric conductors 46. That is to say, the second protective films 48 overlap the second electric conductors 46. Here, the first protective films 47 and the second protective films 48 are connected to one another and form a grid shape.

Walls (wall portions) 51 are arranged on the first protective films 47 and the second protective films 48. The walls 51 extend upward in a height direction from the base 21 outside the regions of the vibration films 24. The vibration films 24 are individually surrounded by the walls 51. The walls 51 form a grid cell for each vibration film 24.

Figure 3:
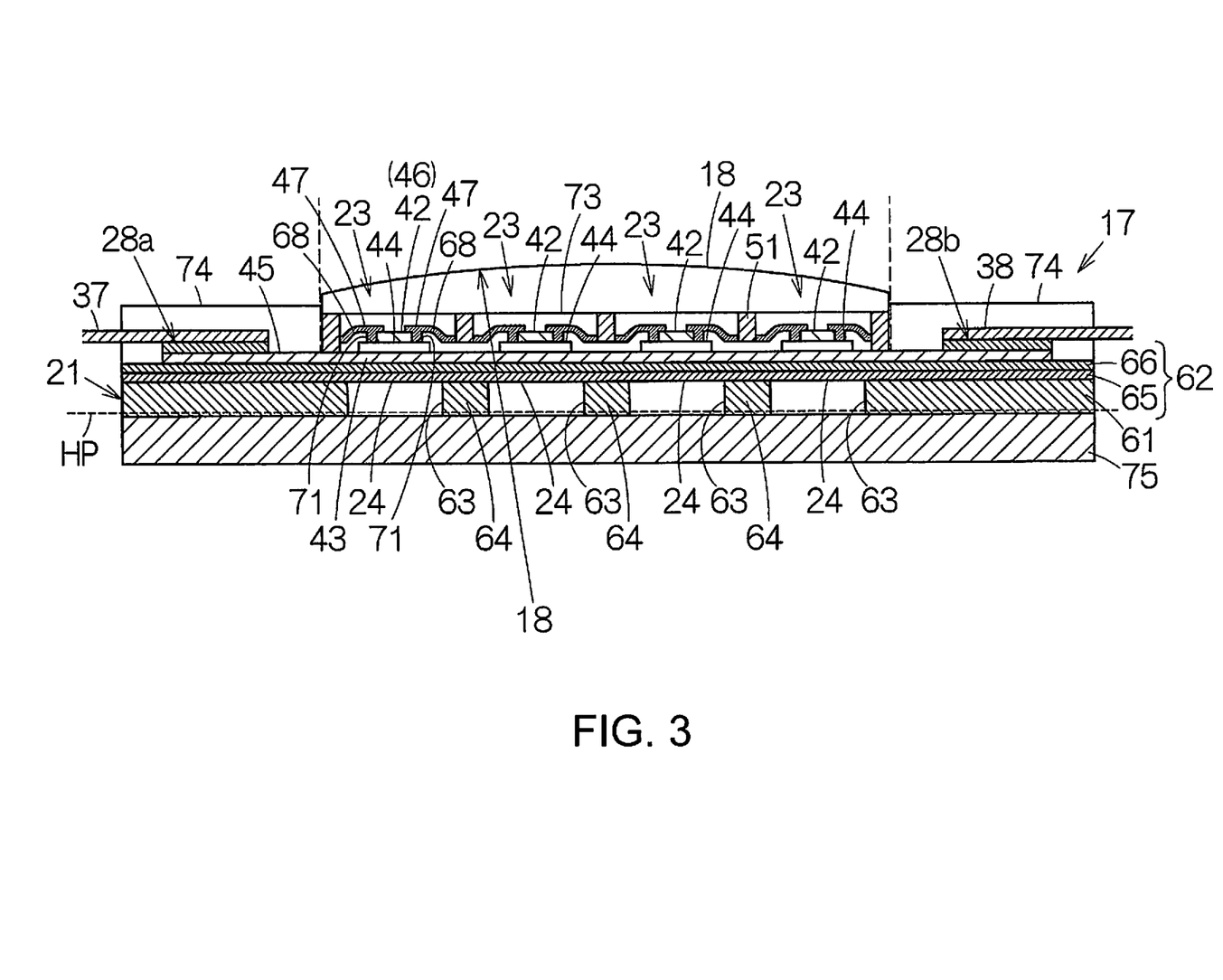
FIG. 3 is a cross-sectional view taken along line A-A in FIG. 1.

As shown in FIG. 3, the base 21 includes a substrate 61 and a coating film 62. The coating film 62 is laminated over the entire surface of the substrate 61. In the substrate 61, an opening 63 is formed for each of the elements 23. The openings 63 define respective spaces that are hollowed out from a back surface of the substrate 61 and that pass through the substrate 61. The openings 63 are arranged in an array in the substrate 61. The outline of a region where the openings 63 are arranged corresponds to the outline of the element array region 25. The substrate 61 can be formed of, for example, a silicon substrate.

A partitioning wall 64 is disposed between every two adjacent openings 63. Adjacent openings 63 are separated from each other by the partitioning walls 64. The wall thickness of the partitioning walls 64 corresponds to the spacing between the openings 63. Each partitioning wall 64 defines two wall surfaces within planes that extend parallel to each other. The wall thickness corresponds to the distance between the two wall surfaces. That is to say, the wall thickness can be defined by the length of a normal line that extends between the wall surfaces orthogonally to the wall surfaces.

The coating film 62 is composed of a silicon oxide ($SiO_2$) layer 65 that is laminated on the surface of the substrate 61 and a zirconium oxide ($ZrO_2$) layer 66 that is laminated on a surface of the silicon oxide layer 65. The coating film 62 is in contact with the openings 63. Thus, portions of the coating film 62 that correspond to the respective outlines of the openings 63 form the vibration films 24. The vibration films 24 refer to those portions of the coating film 62 that face the respective openings 63 and that can thus vibrate in the thickness direction of the substrate 61. The film thickness of the silicon oxide layer 65 can be determined based on resonance frequency.

The bottom electrode 43, the piezoelectric film 44, and the top electrode 42 are sequentially laminated on the surface of each vibration film 24. The piezoelectric film 44 can be formed of, for example, lead zirconate titanate (PZT). Other piezoelectric materials may also be used for the piezoelectric film 44. Here, the piezoelectric film 44 under the corresponding second electric conductor 46 completely covers the first electric conductor 45. The piezoelectric films 44 can serve to avoid short-circuiting of the second electric conductors 46 with the first electric conductors 45.

In this ultrasonic device 17, each second electric conductor 46 has an increased film thickness in regions between adjacent piezoelectric films 44. The film thickness of those regions of the second electric conductor 46 that are located between the piezoelectric films 44 is larger than the film thickness of the first electric conductors 45. Moreover, protective electrically conductive films 68 continuously extend from respective regions of the first electric conductors 45 between adjacent piezoelectric films 44 onto the piezoelectric films 44. The protective electrically conductive films 68 overlap side surfaces of the piezoelectric films 44. In this manner, the protective electrically conductive films 68 protect the side surfaces of the piezoelectric films 44 against moisture, for example.

On each of the piezoelectric films 44, a gap 71 that is in contact with that piezoelectric film 44 is formed between the second electric conductor 46 and the protective electrically conductive film 68. The gap 71 insulates the protective electrically conductive film 68 from the second electric conductor 46. The first protective film 47 occupies the space within the gap 71. Therefore, the protective electrically conductive films 68 are isolated from the second electric conductors 46 (upper electrodes 42) by the first protective films 47.

The acoustic matching layer 73 is laminated over the surface of the base 21. The acoustic matching layer 73 covers the element array 22. The film thickness of the acoustic matching layer 73 is determined in accordance with the resonance frequency of the vibration films 24. For example, a silicone resin film can be used for the acoustic matching layer 73. The acoustic matching layer 73 fits within a space between the first terminal array 28a and the second terminal array 28b. The edges of the acoustic matching layer 73 are spaced apart from the first side 21a and the second side 21b, respectively, of the base 21. The acoustic matching layer 73 has an outline that is smaller than the outline of the base 21.

The acoustic lens 18 is disposed on the acoustic matching layer 73. The acoustic lens 18 is in close contact with a surface of the acoustic matching layer 73. The acoustic matching layer 73 serves to allow the acoustic lens 18 to adhere to the base 21. The partial cylindrical surface 18a of the acoustic lens 18 has generating lines that are parallel to the second electric conductors 46. The curvature of the partial cylindrical surface 18a is determined in accordance with the focus position of ultrasonic waves emitted from a single row of elements 23 connected to a single first electric conductor 45. The acoustic lens 18 may be formed of, for example, a silicone resin. The acoustic lens 18 has an acoustic impedance that is similar to the acoustic impedance of a living body.

A protective film 74 is fixed to the base 21. The protective film 74 may be formed of, for example, a material that is impervious to water, such as an epoxy resin. However, the protective film 74 may also be formed of other resin materials. Preferably, it is desirable that the protective film 74 is made of the same material as the walls 51. The protective film 74 is fixed to side surfaces of the acoustic lens 18 and the acoustic matching layer 73. The protective film 74 overlaps the first electric conductors 45, the second electric conductors 46, and the extraction interconnects 35 on the surface of the base 21 in regions between the acoustic matching layer 73 and the first and second wiring boards 37 and 38. Similarly, the protective film 74 overlaps end portions of the first wiring board 37 and the second wiring board 38 on the base 21.

A backing material 75 is attached to the back surface of the base 21. The back surface of the base 21 is superposed on a surface of the backing material 75. The backing material 75 closes the openings 63 in the back surface of the ultrasonic device 17. The backing material 75 can be provided with a rigid base material. Herein, the partitioning walls 64 are joined to the backing material 75 at their joint surfaces. The backing material 75 is joined to each partitioning wall 64 in at least one joint region. An adhesive can be used to join the backing material 75 to the partitioning walls 64.

Figure 4:
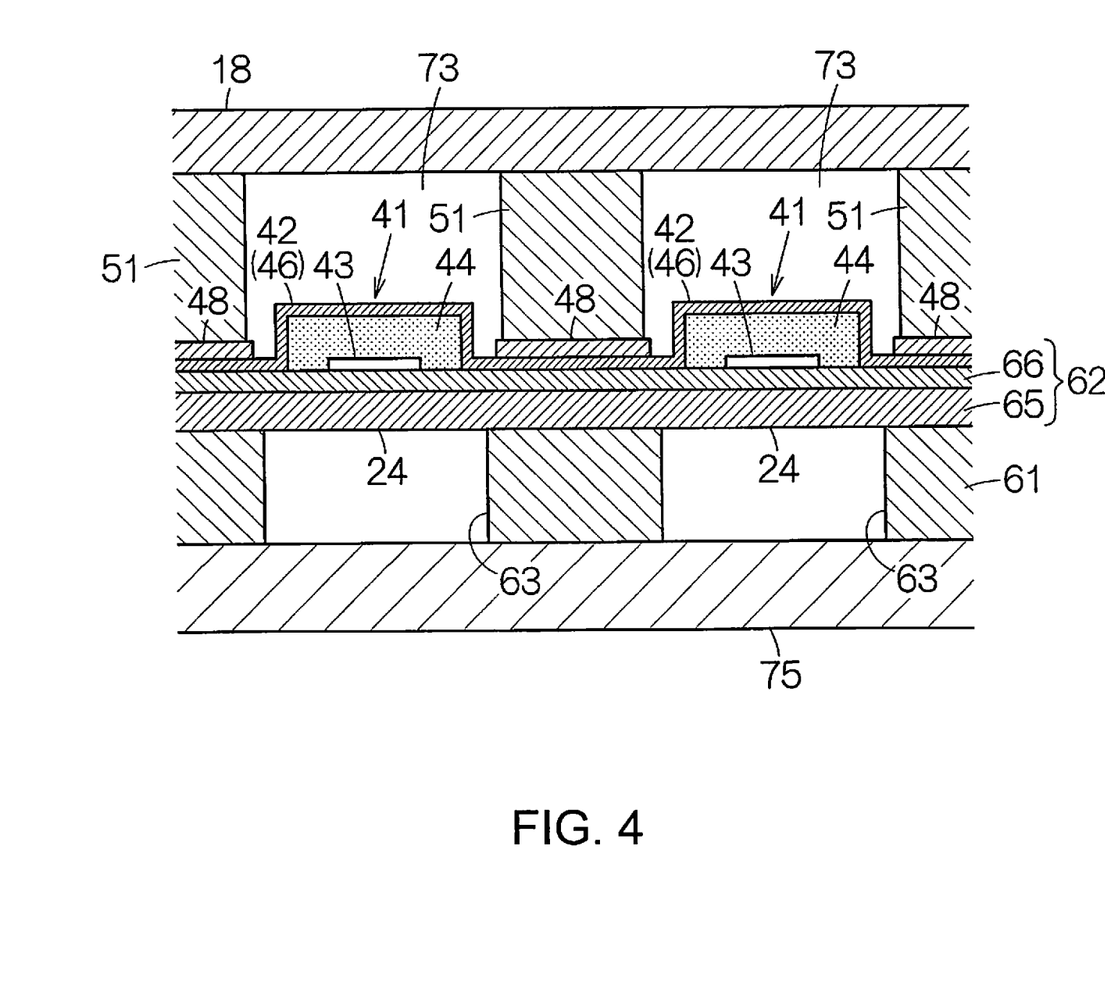
FIG. 4 is an enlarged cross-sectional view taken along line B-B in FIG. 2.

The walls 51 separate portions of the acoustic matching layer 73 that are respectively located on adjacent elements 23 from each other at least in a part of the height range with respect to the height direction from the base 21. Here, the walls 51 extend upward in the height direction from the base 21 for a distance corresponding to the thickness of the acoustic matching layer 73. Top surfaces of the respective walls 51 are joined to the acoustic lens 18. Therefore, each wall 51 divides portions of the acoustic matching layer 73 that are respectively located on adjacent elements 23 from each other. The acoustic impedance of the walls 51 differs from the acoustic impedance of the acoustic matching layer 73. It is sufficient if the walls 51 have a larger acoustic impedance than the acoustic impedance of the acoustic matching layer 73. The walls 51 as well as the first protective films 47 and the second protective films 48 have smaller moisture permeability than the acoustic matching layer 73. Therefore, the walls 51 as well as the first and second protective films 47 and 48 suppress permeation of moisture further than the acoustic matching layer 73 does. To form the above-described walls 51, for example, a baked photoresist film (so-called permanent resist film) can be used for the walls 51. The walls 51 divide the acoustic matching layer 73 in the row direction of the arrangement, that is, in the longitudinal direction of the first electric conductors 45, as shown in FIG. 3, and also divide the acoustic matching layer 73 in the column direction of the arrangement, that is, in the longitudinal direction of the second electric conductors 46, as shown in FIG. 4.

(3) Operation of Ultrasonic Diagnostic Aapparatus

Next, the operation of the ultrasonic diagnostic apparatus 11 will be briefly described. To transmit ultrasonic waves, a pulse signal is supplied to the piezoelectric elements 41 of the elements 23. The pulse signal is supplied to the elements 23 on a row-by-row basis through the bottom electrode terminals 32 and 34 and the top electrode terminals 31 and 33. In each of the elements 23, an electric field acts on the piezoelectric film 44 between the bottom electrode 43 and the top electrode 42. The piezoelectric film 44 vibrates at the frequency of ultrasonic waves. The vibration of the piezoelectric film 44 is transferred to the vibration film 24. Thus, the vibration film 24 vibrates ultrasonically. As a result, a desired ultrasonic beam is emitted toward the subject (for example, the interior of a human body).

Reflected waves of the ultrasonic waves vibrate the vibration film 24 of the element 23. The ultrasonic vibration of the vibration film 24 ultrasonically vibrates the piezoelectric film 44 at a desired frequency. A voltage is output from the piezoelectric element 41 in accordance with the piezoelectric effect of the piezoelectric element 41. In each of the elements 23, a potential is generated between the top electrode 42 and the bottom electrode 43. The generated potentials are output from the bottom electrode terminals 32 and 34 and the top electrode terminals 31 and 33 as electric signals. The ultrasonic waves are detected in this manner.

Ultrasonic waves are repeatedly transmitted and received. As a result, a linear scan or a sector scan is achieved. When the scan is completed, an image is formed based on digital Signals of the output signals. The image thus formed is displayed on the screen of the display panel 15.

To transmit ultrasonic waves, the vibration films 24 vibrate ultrasonically. The ultrasonic vibration is transmitted through the acoustic matching layer 73 and emitted from an interface of the acoustic matching layer 73. The ultrasonic vibration travels across the interface and is transmitted to the acoustic lens 18. At this time, the walls 51 are formed between adjacent elements 23. In accordance with the difference in acoustic impedance, interfaces are formed in the acoustic matching layer 73 at positions between adjacent elements 23. These interfaces prevent transmission of ultrasonic vibration. As a result, transmission of ultrasonic vibration from one ultrasonically vibrating vibration film 24 toward a vibration film 24 of an element 23 adjacent thereto is prevented. When one vibration film 24 is ultrasonically vibrating, ultrasonic crosstalk is prevented. In addition, since the moisture permeability of the first protective films 47 and the second protective films 48 is smaller than that of the acoustic matching layer 73, the first electric conductors 45 and the second electric conductors 46 can be more reliably protected against moisture than in the case where they are covered with the acoustic matching layer 73.

The walls 51 extending in the row direction of the arrangement divide the acoustic matching layer 73 into portions each corresponding to a group of elements 23 that are connected commonly to a single signal line, namely, first electric conductor 45. The vibration films 24 belonging to a group of elements 23 that are connected commonly to a single first electric conductor 45 vibrate simultaneously in response to the supply of a driving signal. A single channel is thus formed. Transmission of ultrasonic vibration from these vibration films 24 toward the vibration films 24 belonging to other groups of elements 23 is prevented. Similarly, the walls 51 extending in the column direction of the arrangement separate portions of the acoustic matching layer 73 from each other, the portions being respectively located on adjacent elements 23 in a group of elements 23 that are connected commonly to a single first electric conductor 45. Transmission of ultrasonic vibration between simultaneously vibrating vibration films 24 is thus prevented. Ultrasonic crosstalk between simultaneously vibrating vibration films 24 is prevented.

(4) Structure of Ultrasonic Device According to Second Embodiment

Figure 5:
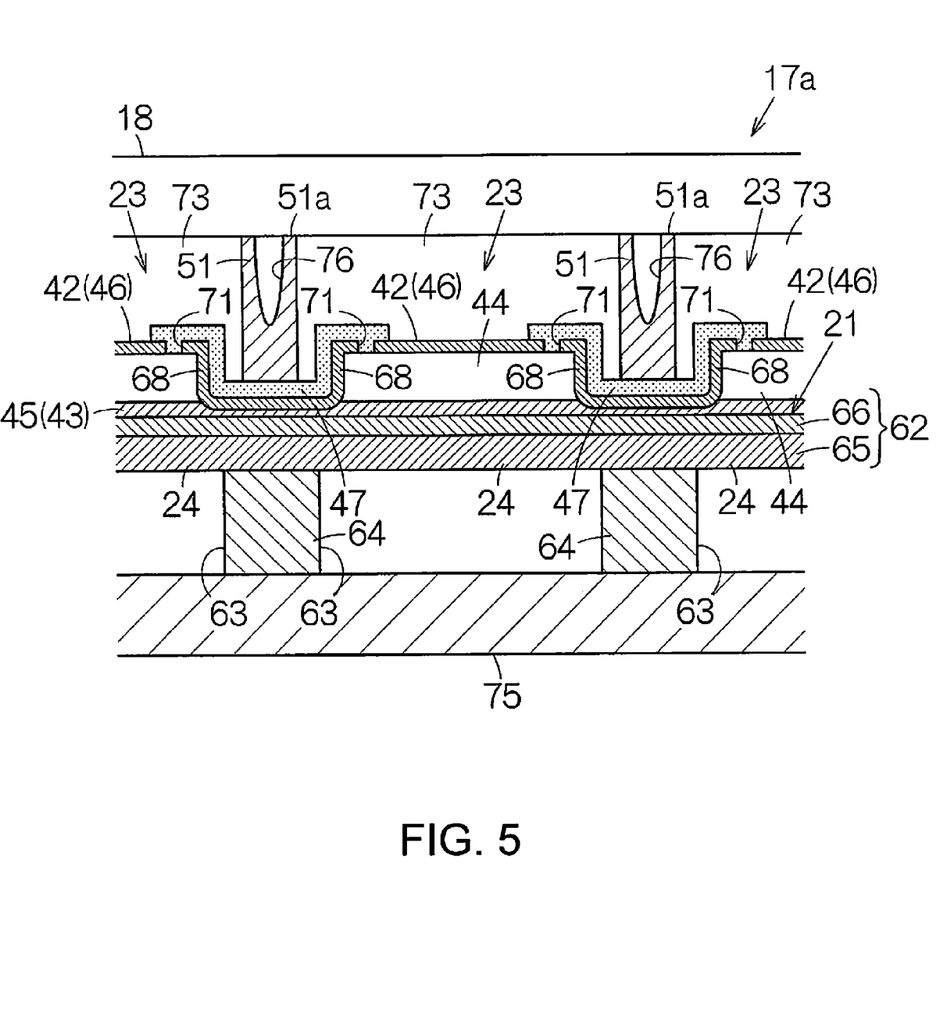
FIG. 5 is a cross-sectional view corresponding to an enlarged partial cross-sectional view of FIG. 3 and schematically showing the structure of an ultrasonic device according to a second embodiment.

FIG. 5 corresponds to FIG. 3 and schematically shows an enlarged cross-sectional view of an ultrasonic device 17a according to a second embodiment. In the ultrasonic device 17a, a cavity 76 is formed in each wall 51. The cavity 76 extends from a top surface 51a of the wall 51 that is farthest from the base 21 with respect to the height direction toward the base 21. However, the cavity 76 ends at an intermediate position without reaching an interface of the wall 51. That is to say, the cavity 76 opens in the top surface 51a of the wall 51, and the bottom of the cavity 76 is located at a predetermined height position from the first protective film 47 with respect to the height direction. Otherwise, the ultrasonic device 17a has the same configuration as the ultrasonic device 17 according to the above-described first embodiment.

The acoustic impedance of the material for the walls 51 differs from the acoustic impedance of the space within the cavity 76. Accordingly, ultrasonic vibration propagates through the wall 51 and is reflected by the interface of the cavity 76. The interface prevents propagation of ultrasonic vibration. As a result, transmission of ultrasonic vibration from a single ultrasonically vibrating vibration film 24 toward the vibration film 24 of an element 23 adjacent thereto is even more reliably prevented. Furthermore, the cavity 76 extends from the top surface 51a of the wall 51 toward the base 21 and ends at an intermediate position without reaching the interface of the wall 51. The cavity 76 does not pass through the wall 51. Since the continuity of the wall 51 at its interfaces with the first protective film 47 and the second protective film 48 is maintained, a sufficient joining strength of the wall 51 with the first protective film 47 and the second protective film 48 can be secured.

Here, a negative photoresist material can be used to form the walls 51. During exposure, the photoresist material in the regions of the walls 51 is exposed to a light beam (or electron beam). Outside the regions of the walls 51, the light beam (or electron beam) is intercepted. At this time, narrow strips are defined in the mask, corresponding to respective regions of the cavities 76. The light beam (or electron beam) is refracted toward spaces underneath the respective strips due to the effect of diffraction. At a position near the surface of the photoresist material, the light beam (or electron beam) is intercepted, but at a position away from the surface, the light beam (or electron beam) enters those spaces underneath the respective strips. As a result, even though each cavity 76 extends from the top surface of the wall 51 toward the base 21, it ends at an intermediate position without reaching the interface (bottom) of the wall 51. After the development, the photoresist material is baked.

(5) Structure of Ultrasonic Device According to Third Embodiment

Figure 6:
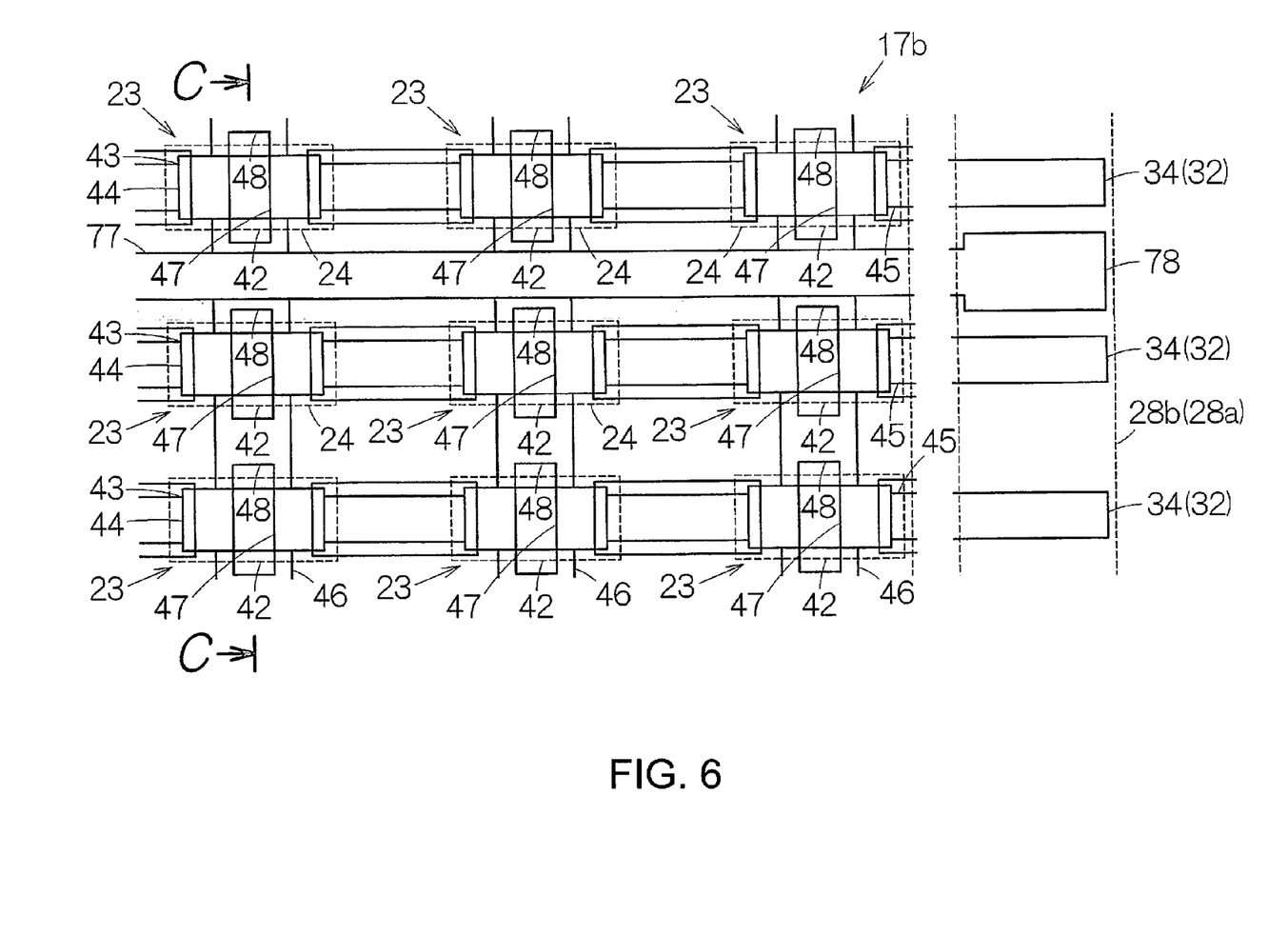
FIG. 6 is an enlarged partial plan view of an ultrasonic device according to a third embodiment.

FIG. 6 schematically shows a plan view of an ultrasonic device 17b according to a third embodiment. In the ultrasonic device 17b, an interconnect pattern (interconnect) 77 made of an electrically conductive material is formed in the row direction of the arrangement of the element array 22 in parallel with the first electric conductors 45. The interconnect pattern 77 is disposed outside the regions of the vibration films 24. The interconnect pattern 77 is spatially separated from the first electric conductors 45. That is to say, the interconnect pattern 77 is electrically isolated from the first electric conductors 45. The interconnect pattern 77 may be formed of an electrically conductive material such as gold, for example. The two ends of the interconnect pattern 77 are respectively connected to top electrode terminals 78. The top electrode terminals 78 are individually arranged between two bottom electrode terminals 32 in the first terminal array 28a and between two bottom electrode terminals 34 in the second terminal array 28b.

Figure 7:
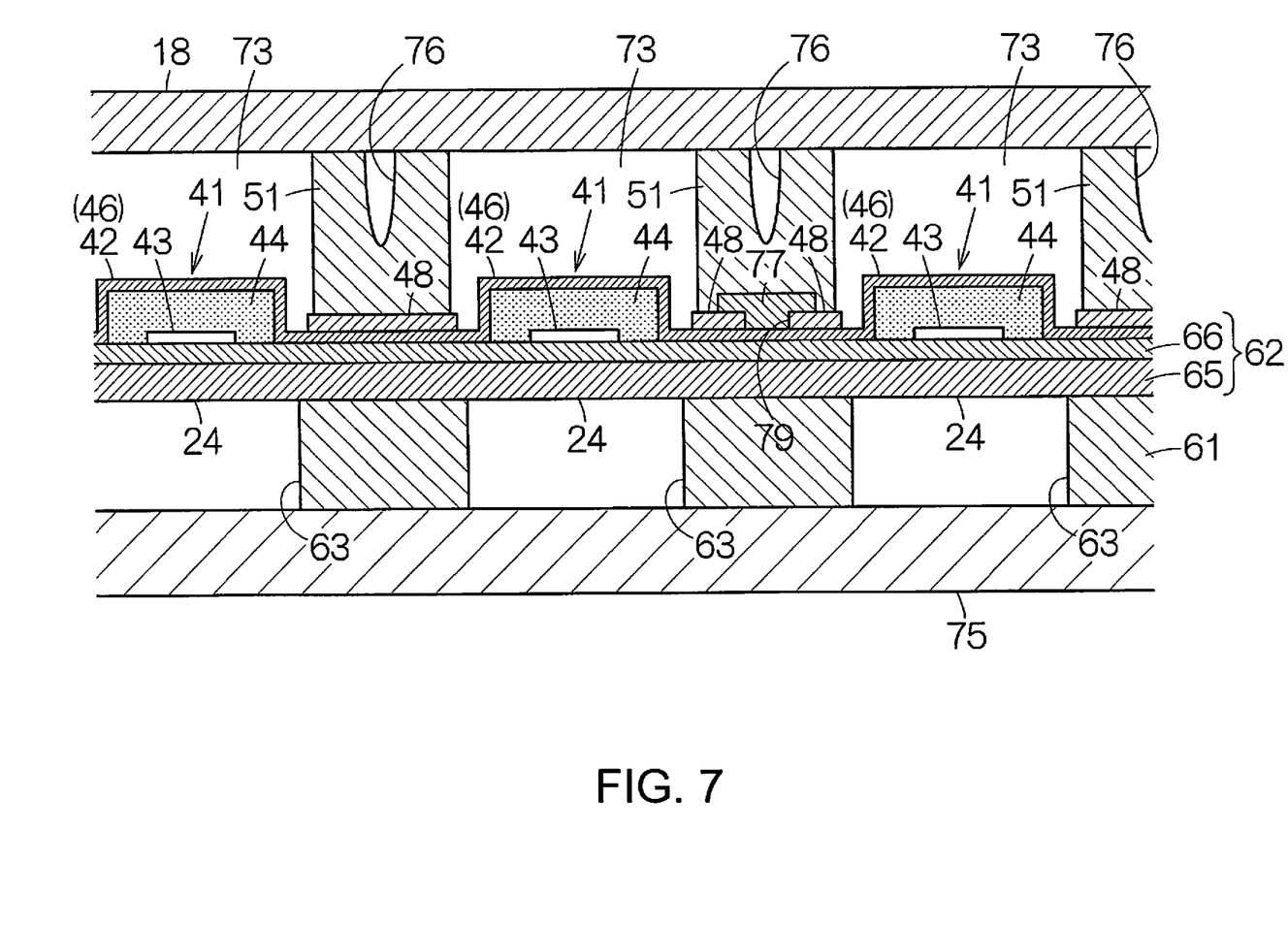
FIG. 7 is a partial cross-sectional view taken along line C-C in FIG. 6.

As is clear from FIG. 6, the interconnect pattern 77 crosses the second electric conductors 46 and extends across the second electric conductors 46. At this time, as shown in FIG. 7, the interconnect pattern 77 is in contact with the second electric conductors 46. Therefore, electrical continuity among the second electric conductors 46 is established. In this manner, for each channel, the top electrodes 42 of the elements 23 are connected to the top electrode terminals 78 via the interconnect pattern 77.

As shown in FIG. 6, when viewed from above, the second protective films 48 are formed at positions on the second electric conductors 46 where the second protective films 48 sandwich portions of the surfaces of the second electric conductors 46. The interconnect pattern 77 is disposed so as to be surrounded by portions of the surfaces of the second electric conductors 46, the second protective films 48 that are arranged at positions where the second protective films 48 sandwich those portions of the surfaces of the second electric conductors 46, and the corresponding wall 51. The interconnect pattern 77 is sealed by the second protective films 48 and the wall 51 over the entire length between the pair of top electrode terminals 78. These second protective films 48, which seal the interconnect pattern 77, demarcate a long, narrow space 79 between the top electrode terminals 78. It is sufficient if the space 79 is continuous over the entire length thereof. As a result, the space 79 crosses the second electric conductors 46 and extends across the second electric conductors 46. Since the space 79 extends across the second electric conductor 46 in this manner, the surfaces of the respective second electric conductors 46 are exposed in the space 79. The interconnect pattern 77 is disposed in this space 79, and thus electrical continuity is secured between the interconnect pattern 77 and each of the second electric conductors 46. Otherwise, the ultrasonic device 17b has the same configuration as the first embodiment or the second embodiment.

The interconnect pattern 77 connects the spatially separated second electric conductors 46 to one another. At this time, the interconnect pattern 77 is sealed over the entire length thereof. The interconnect pattern 77 is thus protected.

Although some embodiments of the invention have been described in detail above, a person skilled in the art will readily understand that various modifications may be made without substantially departing from the novel teachings and the effects of the invention. Therefore, such modifications are entirely included within the scope of the invention. For example, any term described at least once together with a broader or synonymous different term in the specification or the drawings may be replaced by the different term at any place in the specification or the drawings. Moreover, the configurations and operations of the ultrasonic diagnostic apparatus 11, the ultrasonic probe 13, the ultrasonic devices 17, 17a, 17b, the elements 23, the piezoelectric elements 41, and the like are not limited to those described in the foregoing embodiments, but may be modified in various manners.

The entire disclosure of Japanese Patent Application No. 2014-155713 filed on 7/31/2014 is expressly incorporated by reference herein.

What is claimed is:

1. An ultrasonic device, comprising:
   a base;
   ultrasonic transducer elements that are arranged in an array on the base and that have respective vibration films;
   an acoustic matching layer formed on the individual ultrasonic transducer elements;
   electric conductors that are arranged between adjacent ultrasonic transducer elements of said ultrasonic transducer elements when viewed from above in a thickness direction of the base and that are connected to electrodes of said ultrasonic transducer elements;

protective films that are arranged on the electric conductors and that have smaller moisture permeability than the acoustic matching layer; and wall portions that are arranged on the protective films and that separate portions of the acoustic matching layer that are respectively located on the adjacent ultrasonic transducer elements from each other at least in a part of a height range with respect to a height direction from the base, the wall portions having an acoustic impedance that is different from an acoustic impedance of the acoustic matching layer.

2. The ultrasonic device according to claim 1, wherein the protective films are arranged at positions on the electric conductors where the protective films sandwich portions of surfaces of the electric conductors when viewed from above in the thickness direction of the base, and the ultrasonic device further comprises:

an interconnect that is disposed so as to be surrounded by the portions of the surfaces of the electric conductors, the protective films that are arranged at positions where the protective films sandwich the portions of the surfaces of the electric conductors, and the corresponding wall portion.

3. The ultrasonic device according to claim 1, wherein a cavity is formed in each of the wall portions.

4. The ultrasonic device according to claim 3, wherein the cavity opens in a top surface of the wall portion that is farthest from the base with respect to the height direction, and a bottom of the cavity is located at a predetermined height position from the protective film with respect to the height direction.

5. The ultrasonic device according to claim 1, wherein the protective films are oxide films or nitride films of an inorganic material.

6. The ultrasonic device according to claim 5, wherein the protective films are formed of $Al_2O_3$.

7. The ultrasonic device according to claim 1, wherein the wall portions are formed of a material having smaller moisture permeability than the acoustic matching layer.

8. The ultrasonic device according to claim 7, wherein the wall portions are formed of a permanent resist film.

9. The ultrasonic device according to claim 1, wherein the wall portions divide the acoustic matching layer into portions each corresponding to a group of the ultrasonic transducer elements that are connected commonly to a single signal line.

10. The ultrasonic device according to claim 9, wherein the wall portions separate portions of the acoustic matching layer from each other, the portions being respectively located on the adjacent ultrasonic transducer elements contained in the group of the ultrasonic transducer elements that are connected commonly to the signal line.

11. A probe, comprising:

the ultrasonic device according to claim 1; and a housing that supports the ultrasonic device.

12. An electronic apparatus, comprising:

the ultrasonic device according to claim 1; and a processor that is connected to the ultrasonic device and that processes an output from the ultrasonic device.

13. An ultrasonic imaging apparatus, comprising:

the ultrasonic device according to claim 1; and a display device that displays an image generated based on an output from the ultrasonic device.

14. An ultrasonic device, comprising:

a base;

ultrasonic transducer elements that are arranged in an array on the base and that have vibration films;

an acoustic matching layer formed on the ultrasonic transducer elements;

electric conductors that are arranged between adjacent ultrasonic transducer elements of said ultrasonic transducer elements;

protective films that are arranged on the electric conductors and that have smaller moisture permeability than the acoustic matching layer; and wall portions that are arranged on the protective films and that separate adjacent portions of the acoustic matching layer from each other, wherein an acoustic impedance of the wall portions is different from an acoustic impedance of the acoustic matching layer.

* * * * *